United States Patent [19]

Baiocchi

[11] 4,001,219
[45] Jan. 4, 1977

[54] STEROIDAL DERIVATIVES OF BENDAZOLIC ACID AND PROCESS FOR THE PREPARATION OF THE SAME

[76] Inventor: Leandro Baiocchi, via Platina, 22 Rome, Italy

[22] Filed: Jan. 9, 1976

[21] Appl. No.: 647,749

[30] Foreign Application Priority Data

Feb. 13, 1975  Italy .................................. 48150/75

[52] U.S. Cl. ......................... 260/239.5; 260/397.45
[51] Int. Cl.$^2$ ......................................... C07J 5/00
[58] Field of Search ..................... 260/239.5, 397.45

[56] References Cited

UNITED STATES PATENTS 3,787,454  1/1974  Kerb et al. ..................... 260/397.45

FOREIGN PATENTS OR APPLICATIONS 919,830    2/1963  United Kingdom .......... 260/397.45
1,272,841  5/1972  United Kingdom .......... 260/397.45

*Primary Examiner*—Elbert L. Roberts
*Attorney, Agent, or Firm*—Robert E. Burns; Emmanuel J. Lobato; Bruce L. Adams

[57] ABSTRACT

Esters of [(1-benzyl-1H-indazol-3-yl)-oxy]acetic acid at primary hydroxyl in position 21 of hydrocortisone, cortisone, prednisone and prednisolone, and process for the preparation of the same.

2 Claims, No Drawings

STEROIDAL DERIVATIVES OF BENDAZOLIC ACID AND PROCESS FOR THE PREPARATION OF THE SAME

The object of this invention are some esters of [(1-benzyl-1H-indazol-3-yl)-oxy]acetic acid (generic name: Bendazac) at primary hydroxyl of corticosteroids having genera formula (I)

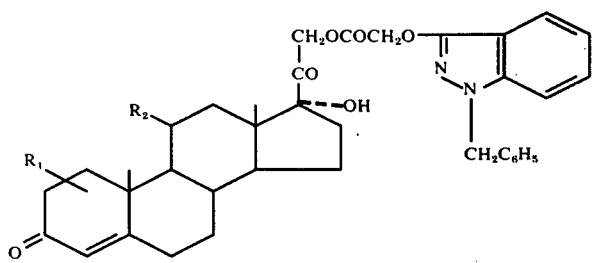

(I)

where $R_1$ = a single or a double bond, and $R_2$ = OH or O.

In particular, this invention deals with four derivatives of Bendazac, with hydrocortisone, with cortisone, with prednisone and with prednisolone. These substances show a spectrum of anti-inflammatory effects which had never been found before in other drugs. In fact, they inhibit a wide band of pathologic responses ranging from the prevailingly productive and vascular ones (which, as such, are especially sensitive to corticosteroids) and those having a degenerative and necrotic character (which are sensitive to Bendazac). Their effects, on the other hand, do not even correspond to those obtained with combinations of drugs showing a qualitatively different action and it can be stated that the substances claimed by this invention show a character of their own as regards their pharmacological effects. The uses are foreseen especially in the topical field in dermatology and a system therapeutic use is also foreseen, especially in the rheumatic and allergic diseases.

As regards the process of preparation, the most convenient consists in the reaction between the steroid (cortisone, hydrocortisone, prednisone or prednisolone) and [(1-benzyl-1H-indazol-3-yl)-oxy]acetyl chloride in the presence of an HCl acceptor.

Pyridine (which is used also as acid acceptor), benzene, chloroform, dioxane, dimethylformamide, dimethoxyethane, acetone, cellosolve and other similar substances can be used as solvents, while pyridine, triethylamine and quinoline are preferably used as acid acceptors.

[(1-benzyl-1H-indazol-3-yl)-oxy]-acetyl chloride, which is not described in the literature, is prepared from the corresponding acid by action of thionyl chloride, of phosphorous oxychloride or pentachloride.

We are reporting herebelow, as a non-restrictive example, the preparation of the ester with hydrocortisone (21-ester of 11β, 17α, 21-trihydroxy-pregn-4-ene-3,20-dione with [(1-benzyl-1H-indazol-3-yl)-oxy]acetic)acid.

EXAMPLE 1

[(1-benzyl-1H-indazol-3-yl)-oxy]acetyl chloride

[(1-benzyl-1H-indazol-3-yl)-oxy]acetic acid (Bendazac) (50 g) are suspended in benzene (500 ml) and thionyl chloride (15 ml) is added. The solution is stirred under reflux for about half an hour, cooled, concentrated at room temperature under reduced pressure, the oily residue is treated with further benzene and concentrated again to dryness under vacuum. After addition of hexane, the acidic chloride precipitates as lightly coloured crystals. The solution is filtered and washed with hexane. The substance is colourless and shows m.p. 78°–9°. Yield: 90% of the calculated.

EXAMPLE 2

21-ester of [(1-benzyl-1H-indazol-3-yl-oxy]-acetic acid with 11β, 17α, trihydroxy-pregn-4-ene-3,20-dione (ester of Bendazac with hydrocortisone)

Hydrocortisone (25 g) and Bendazac chloride (21 g) are suspended in anhydrous dioxane (250 ml). Pyridine (6 ml) is added and the solution is kept under stirring for 2 hours at room temperature. Pyridine hydrochloride which separates is filtered and the clear dioxane solution is added, under strong stirring, to a solution of sodium bicarbonate (20 g) in distilled water (2500 ml). The colourless precipitate which is formed is filtered, washed with water and dried on a porous plate. The substance crystallizes from ethanol. Needles. m.p. 174°–6°. Yield: 75%.

Bendazac ester with cortisone (m.p. 145°–7° from ethanol), with prednisone (m.p. 167°–9° from ethanol) and with prednisolone (m.p. 187°–9° from ethanol) are also prepared similarly to what is described in example 2.

I claim:

1. Esters of [(1-benzyl-1H-indazol-3-yl)-oxy]-acetic acid at primary hydroxyl in position 21 of hydrocortisone, cortisone, prednisone and prednisolone.

2. Process for the preparation of the esters mentioned in claim 1, characterized by the fact that cortisone, hydrocortisone, prednisone and prednisolone are reacted at room temperature with [(1-benzyl-1H-indazol-3-yl)-oxy]acetyl chloride in the presence of an HCl acceptor.

* * * * *